United States Patent
Denyer et al.

(10) Patent No.: US 8,607,786 B2
(45) Date of Patent: Dec. 17, 2013

(54) INHALATION METHOD AND APPARATUS (75) Inventors: Jonathan S. H. Denyer, Chichester (GB); Ivan R. Prince, Chichester (GB); Anthony Dyche, Hayling Island (GB)

(73) Assignee: Respironics Ltd, West Sussex (GB)

( * ) Notice: Subject to any disclaimer, the term of this patent is extended or adjusted under 35 U.S.C. 154(b) by 1687 days.

(21) Appl. No.: 10/535,867

(22) PCT Filed: Nov. 20, 2003

(86) PCT No.: PCT/GB03/05058
§ 371 (c)(1),
(2), (4) Date: Oct. 21, 2005

(87) PCT Pub. No.: WO2004/045690
PCT Pub. Date: Jun. 3, 2004

(65) Prior Publication Data
US 2007/0125370 A1    Jun. 7, 2007

(30) Foreign Application Priority Data
Nov. 20, 2002 (GB) .................................. 0227106.2

(51) Int. Cl.
A61M 16/00    (2006.01)
A61M 15/00    (2006.01)
B05D 7/14     (2006.01)
B65D 83/06    (2006.01)

(52) U.S. Cl.
USPC ............. 128/203.15; 128/200.14; 128/203.12

(58) Field of Classification Search
USPC ............. 128/200.14, 200.21, 203.15, 204.26, 128/202.22, 203.12, 204.23
See application file for complete search history.

(56) References Cited

U.S. PATENT DOCUMENTS

| 4,677,975 | A |   | 7/1987  | Edgar et al. |
|-----------|---|---|---------|--------------|
| 5,333,106 | A | * | 7/1994  | Lanpher et al. ............. 600/538 |
| 5,363,842 | A | * | 11/1994 | Mishelevich et al. ..... 128/200.14 |
| 5,404,871 | A |   | 4/1995  | Goodman et al. |
| 5,450,336 | A | * | 9/1995  | Rubsamen et al. ........... 702/104 |
| 5,713,349 | A |   | 2/1998  | Keaney |

(Continued)

FOREIGN PATENT DOCUMENTS

| EP | 0 824 023 A1 | 2/1998 |
| EP | 0 627 266 B1 | 8/1999 |

(Continued)

Primary Examiner — Justine Yu
Assistant Examiner — Colin W Stuart
(74) Attorney, Agent, or Firm — Timothy A. Nathan (57) ABSTRACT A drug delivery apparatus of the type which releases a drug in aerosolized form into the inhaled airstream of a person, programmed to release the drug in a pulse which ends a pre-set time before the person is expected to stop inhaling. In doing so, a minimum residence time within the lungs is created, and drug treatment time can be reduced. A corresponding method of controlling a drug delivery apparatus comprises the step of controlling the apparatus to release the drug in aerosolized form into the inhaled airstream of a person in a pulse which ends a pre-set time before the person is expected to stop inhaling.

24 Claims, 6 Drawing Sheets

(56) References Cited

U.S. PATENT DOCUMENTS

| | | | |
|---|---|---|---|
| 5,906,202 A | 5/1999 | Schuster et al. | |
| 6,119,953 A | 9/2000 | Ganan-Calvo et al. | |
| 6,240,920 B1* | 6/2001 | Strom | 128/204.23 |
| 6,739,332 B1* | 5/2004 | Higenbottam et al. | 128/200.13 |
| 6,820,618 B2* | 11/2004 | Banner et al. | 128/204.23 |
| 6,845,770 B2* | 1/2005 | Klimowicz et al. | 128/200.16 |
| 7,073,499 B1* | 7/2006 | Reinhold et al. | 128/200.18 |
| 2001/0022279 A1* | 9/2001 | Denyer et al. | 206/438 |
| 2002/0104532 A1 | 8/2002 | Christrup et al. | |
| 2002/0153006 A1* | 10/2002 | Zimlich et al. | 128/200.14 |
| 2003/0205229 A1* | 11/2003 | Crockford et al. | 128/204.23 |

FOREIGN PATENT DOCUMENTS

| | | |
|---|---|---|
| EP | 1 142 600 A1 | 10/2001 |
| EP | 0 910 421 B1 | 3/2003 |
| GB | 2 320 900 A | 7/1998 |
| WO | WO 94/17370 | 8/1994 |
| WO | WO 99/63946 | 12/1999 |
| WO | WO 00/24445 A1 | 5/2000 |
| WO | WO 00/38770 A3 | 7/2000 |
| WO | WO 00/50111 | 8/2000 |
| WO | WO 01/58514 A1 | 8/2001 |
| WO | WO 02/09574 A2 | 2/2002 |
| WO | WO 02/058771 A1 | 8/2002 |
| WO | WO 03/059423 A1 | 7/2003 |

* cited by examiner

TO MOUTHPIECE

ELECTRONIC CONTROL 62

POWER SUPPLY 61

AIR FLOW DETECTOR 68

PROCESSOR 70

AEROSOL GENERATOR 72

PATIENT SIGNALLING DEVICE (VIBRATION OR AUDIO) 73

INHALATION METHOD AND APPARATUS

The present invention relates to drug delivery apparatus of a type which releases the drug in aersolized form into the inhaled airstream of a person.

A number of devices are available for delivering a drug into the lungs of a patient. A pneumatic or jet type nebulizer is particularly effective in supplying an aerosolized drug for inhalation, but other types of nebulizer are also available, such as ultrasonic type nebulizers in which the drug to be atomized is forced through a mesh by vibration of a piezoelectric crystal, whereupon the droplets passing through the mesh are entrained in the air being inhaled by the patient. The gauge of the mesh determines the size of the droplets which enter the airstream. Electrohydrodynamic (EHD) nebulizers and capillary micro jet nebulizers are also known. Alternatively, a dosimetric spacer can be used. When using a spacer, the drug is introduced into a holding chamber of the spacer, either in aerosolized form, or by loading the air within the holding chamber with the drug in powdered form. The patient breathes from the holding chamber thereby inhaling the drug laden air. Such spacers are particularly effective when treating children or elderly patients, and for use with certain drugs. The drug is normally delivered over a number of breaths.

An example of a mesh type nebulizer is shown in WO 99/63946, and examples of EHD and capillary micro jets nebulizers can be found in WO 00/38770 and U.S. Pat. No. 6,119,953 respectively, and we hereby import these disclosures in their entirety by this reference.

A pneumatic nebulizer is shown in EP 0627266 A2 in which air from a pressurized air source issues from an air outlet hole around which are disposed holes through which the liquid to be atomized is drawn out from a main reservoir. Each of these holes is within a groove forming a secondary reservoir around the air outlet hole. A deflector bar is located across and in the path of the air issuing from the air outlet so that as it issues from the air outlet, it is immediately deflected across the top of the liquid outlet holes thereby creating low pressure regions drawing the liquid up from the main reservoir beneath, and atomizing that liquid as it is drawn from the holes. The droplets generated in this way are carried to the patient for inhalation. Atomization can be switched on and off by switching on and off the pressurized air supply to the nebulizer.

European patent publication number 0910421 discloses a nebulizer, manufactured under the name Halolite, which delivers a drug during the first half of the patients inhalation in order to maximise lung deposition. The apparatus is interactive in that it measures the duration of a patient's inhalation and calculates a time period that is one half of an average of the patient's duration of inhalation. It is therefore able to match the delivery of the drug with the inhalation profile of the patient and takes account of changes in the patient's inhalation duration over time. It does not require the patient to perform a specific inhalation manoeuvre. The entire disclosure of EP 0910421 is hereby incorporated into this specification by this reference.

A drug delivery system described in WO98/52633, called the Akita system is known in which aerosolized drug is delivered to a patient in an airstream under a positive pressure delivered at 15 liters per minute up to a volume equivalent to 80% respiratory capacity. Respiratory capacity is defined as the inhalation volume measured from the end of a normal tidal exhalation to maximum lung capacity. The system includes controlled inhalation flow which prevents air from being delivered more quickly. This has the effect of lengthening the duration of inhalation. The system directs the patient when to breathe in, when to hold his breath, and when to exhale. Thus, it is arranged such that the patient, upon filling his lungs to capacity with air is instructed by the system to hold his breath for a period typically of the order of 5 to 9 seconds. The patient is then indicated to exhale. This breathing pattern is repeated until the drug has been completely delivered. Such a system is effective in delivering a high proportion of the drug to the lungs since the residence time of the drug in the lungs is relatively long, in this case at least 5 seconds, and for most of the drug rather longer than this. As a result, on exhalation, most of the drug has sedimented within the lungs such that it will not be exhausted from the lungs during exhalation.

However, the Akita system must first be set up with the patient in a clinic since the system must know the respiratory capacity of the patient in order to indicate the beginning of the breath hold step at the appropriate time. Different patients will have very different respiratory capacities depending on various factors including age, body size and the effect of any respiratory diseases. In addition, the duration of the breath hold must also be customised for particular patients to ensure that the patient will not suffer distress during the use of the system. If the breath hold is too long, then the patient will be unable to continue the treatment over a number breaths without suffering such distress. In addition, as the patient's symptoms change, then the system will need to be reconfigured to take account of this by another visit to a clinic.

According to a first aspect of the present invention, a drug delivery apparatus of the type which releases the drug in aerosolized form into the inhaled airstream of a person is programmed to release the drug in a pulse which ends at a pre-set time before the person is expected to stop inhaling to effect an aerosol hold in which the minimum lung residence time is at least 0.5 s.

By ensuring that the minimum residence time within the lung is of a certain length, the amount of the drug which can be exhaled is minimised since sedimentation of the drug becomes a significant factor provided that the residence time is sufficiently great.

It is preferred that the aerosol hold gives a minimum lung residence time of about 1 s.

It is preferred that the drug delivery apparatus is programmed to release the drug in a pulse in a pre-set proportion of the expected period of inhalation, in the event that a breathing threshold is not reached. The breathing threshold may be a minimum expected duration of inhalation, and/or a minimum tidal volume during inhalation. The minimum expected duration of inhalation may be about twice the pre-set time before the person is expected to stop inhaling when the pulse ends. The minimum tidal volume may be about 1 liter.

It is preferred that the pre-set time is between 0.5 seconds and 2.0 seconds, preferably between 0.75 seconds and 1.5 seconds, and most preferably about 1 second.

According to one embodiment, the apparatus farther comprises an airflow sensor which senses the person's inhaled airstream. The apparatus may further include a memory for holding any one or more of the following:

(i) the duration of inhalation of a number of recent inhalations;

(ii) the average duration of inhalation of a number of recent inhalations;

(iii) the pre-set time before the person is expected to stop inhaling;

(iv) the breathing threshold;

(v) programming instructions on the operation of the apparatus.

The apparatus may also include a processor for controlling the operation of the apparatus, and for calculating the length of the pulse of release of the drug. A timer might also be included.

The aerosol delivery is ceased preferably at least half a second before the person is expected to stop inhaling, and most preferably about one second before.

According to a second aspect of the invention, a method of controlling drug delivery apparatus of the type which releases the drug in aerosolized form into the inhaled airstream of a person comprises: controlling the apparatus to release the drug in aerosolized form into the inhaled airstream of a person in a pulse which ends at a pre-set time before the person is expected to stop inhaling to effect an aerosol hold in which the minimum lung residence time is at least 0.5 s.

Preferably, the aerosol hold gives a minimum lung residence time of about 1 s.

It is preferred that the method further comprise the step of creating an estimate of the duration of inhalation. From this, the pre-set time can be determined.

According to one embodiment, the creating of an estimate of the duration of inhalation includes timing the duration of inhalation of one or more earlier breaths. Where more than one earlier breath is timed, an average of those breaths, typically three or four breaths, is taken.

If a breathing threshold is not reached, the drug is released in a pulse for a pre-set proportion of the expected period of inhalation. The breathing threshold may be a minimum expected duration of inhalation, and in the preferred arrangement, the minimum expected duration of inhalation is about twice the pre-set time before the person is expected to stop inhaling when the pulse ends. Alternatively, the breathing threshold is a minimum tidal volume, preferably about 1 liter.

Preferably, the pre-set time is between 0.5 seconds and 2 seconds, more preferably between 0.75 seconds and 1.5 seconds, and most preferably about 1 second.

The method preferably comprises sensing the person's inhaled airstream.

According to a third aspect of the invention, the use of a drug delivery apparatus according to the first aspect of the invention with a drug in the manufacture of the drug in aerosolized form for use in the treatment of any one of the following conditions: asthma, COPD, cystic fibrosis, primary pulmonary hypertension, A1AT deficiency, lung transplantation, lung cancer.

According to a fourth aspect of the invention, the release of a drug in aerosolised form into the inhaled airstream of a person in a pulse which ends at a pre-set time before the person is expected to stop inhaling to effect an aerosol hold in which the minimum lung residence time is at least 0.5 s.

The apparatus in one embodiment includes an airflow regulator for restricting the speed of the inhaled airstream through the device.

The invention will now be described by way of example only with reference to the drawings in which.

EXPERIMENT

The Akita and Halolite system described in the introductory part of this application were used in an experiment in which a patient was supplied with a radio labelled aerosol. The aerosol was radio labelled to allow scintigraphic evaluation of the experiment. The systems were used in accordance with the manufacturer's recommendations. A Sidestream nebulizer (Profile Respiratory Systems Ltd, Bognor Regis UK) and a nose clip were used. The Akita system provided a positive pressure stream of air for inhalation at 15 liters per minute up to a volume equivalent to 80% of respiratory capacity with a breath hold of between 5 and 9 seconds. A computer screen provided feedback to the patient as to the duration of inhalation and the breath holding pause required. In the case of the Akita System, on commencement of inhalation, the computer screen displays a numerical countdown of the period over which the patient should inhale. At the end of that period of time, the person must hold his breath while the computer screen displays a further countdown of time until the patient is permitted to exhale. In the case of the Halolite System, the patient breathes in and out naturally without any feedback indicating to the person when to start inhaling, stop inhaling or carry out a breath hold. In fact, with the Halolite, since the person is intended to breathe in a slow relaxed manner, there will not be any breath hold period. However, since the atomisation stops before the end of the breath, there is a period of time during which the patient is still inhaling, but no aerosol is reaching the person's lungs. This period of time is referred to in this specification as the "aerosol hold time". This contrasts with the Akita System in which atomisation occurs during the entire inhalation phase, and only stops once the patient begins his breath hold. Therefore, the aerosol hold time and the breath hold time are rather different, but have the same effect of defining a minimum period during which the aerosol is resident within the lung. After the breath hold the subject exhales through a filter in order to trap any of the aerosol.

A treatment time of between 5 and 12 minutes was needed to deliver a set dose of 0.4 ml of Tc-DTPA from a 2.5 ml nebulizer fill.

Figure 1:
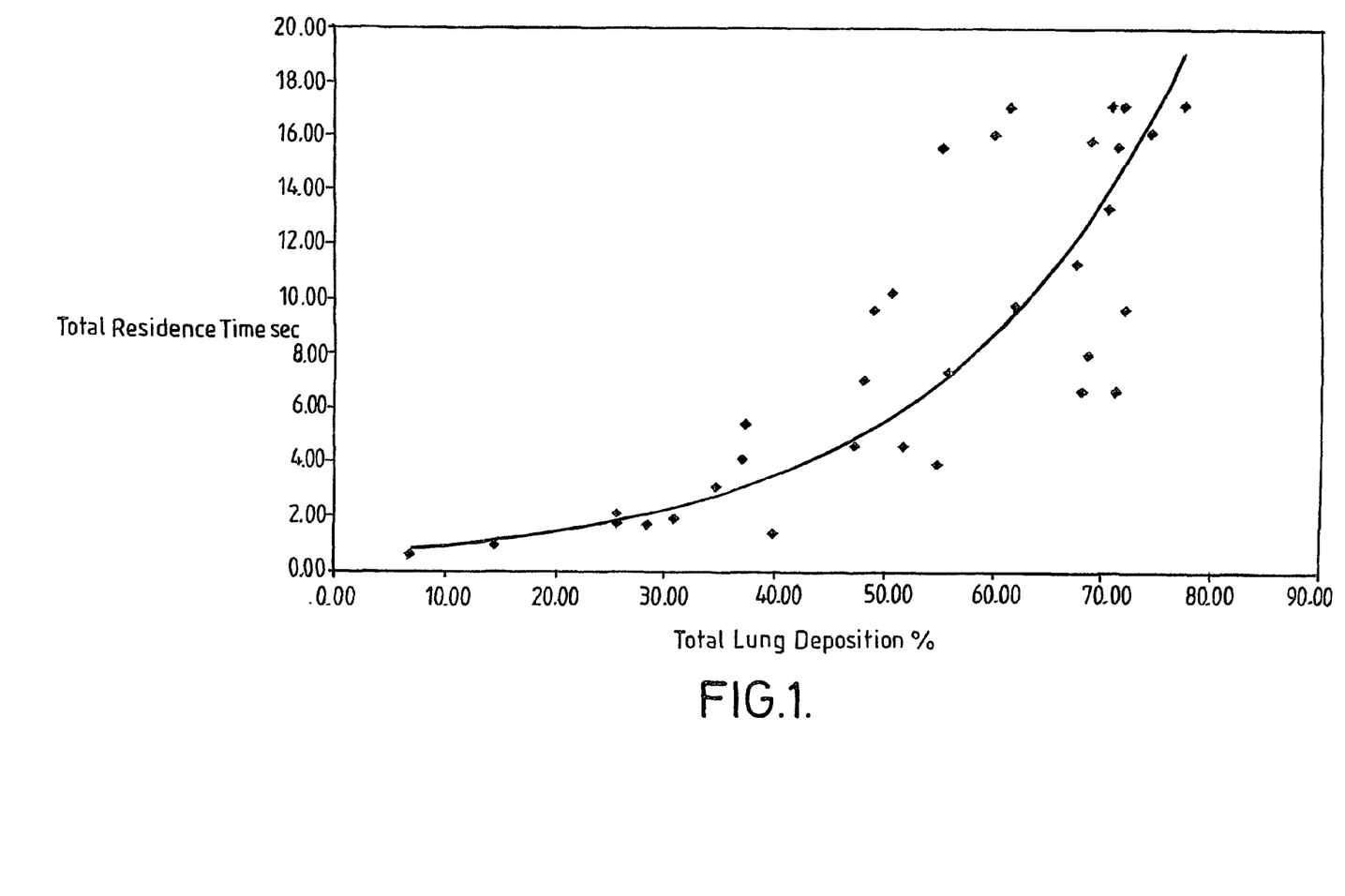
FIG. 1 is a graph in which the total residence time of a drug within the lungs is plotted against the percentage of the drug which is deposited within the lungs.
Figure 2:
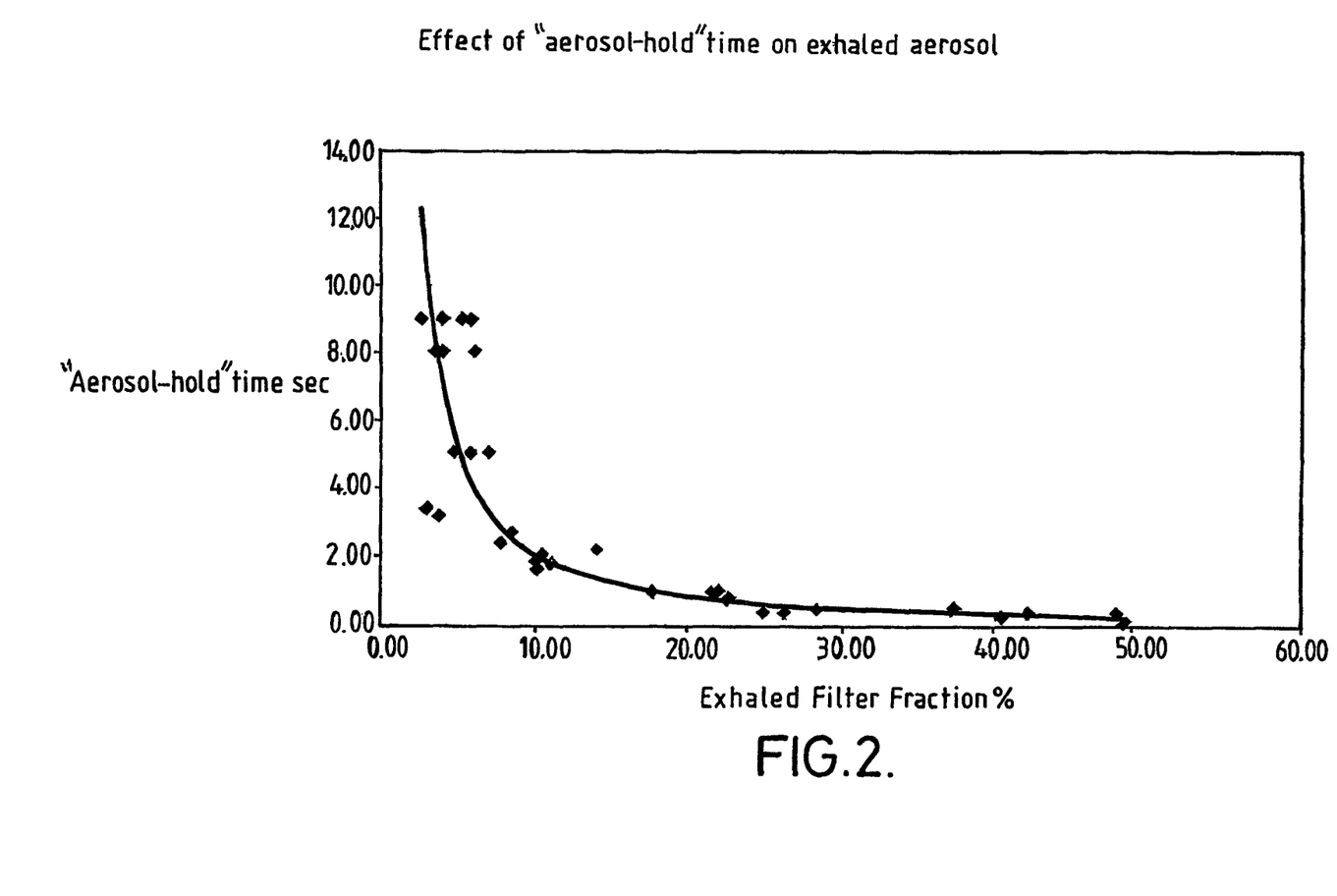
FIG. 2 is a graph plotting the aerosol hold/breath hold time against exhaled filter fraction.
Figure 3:
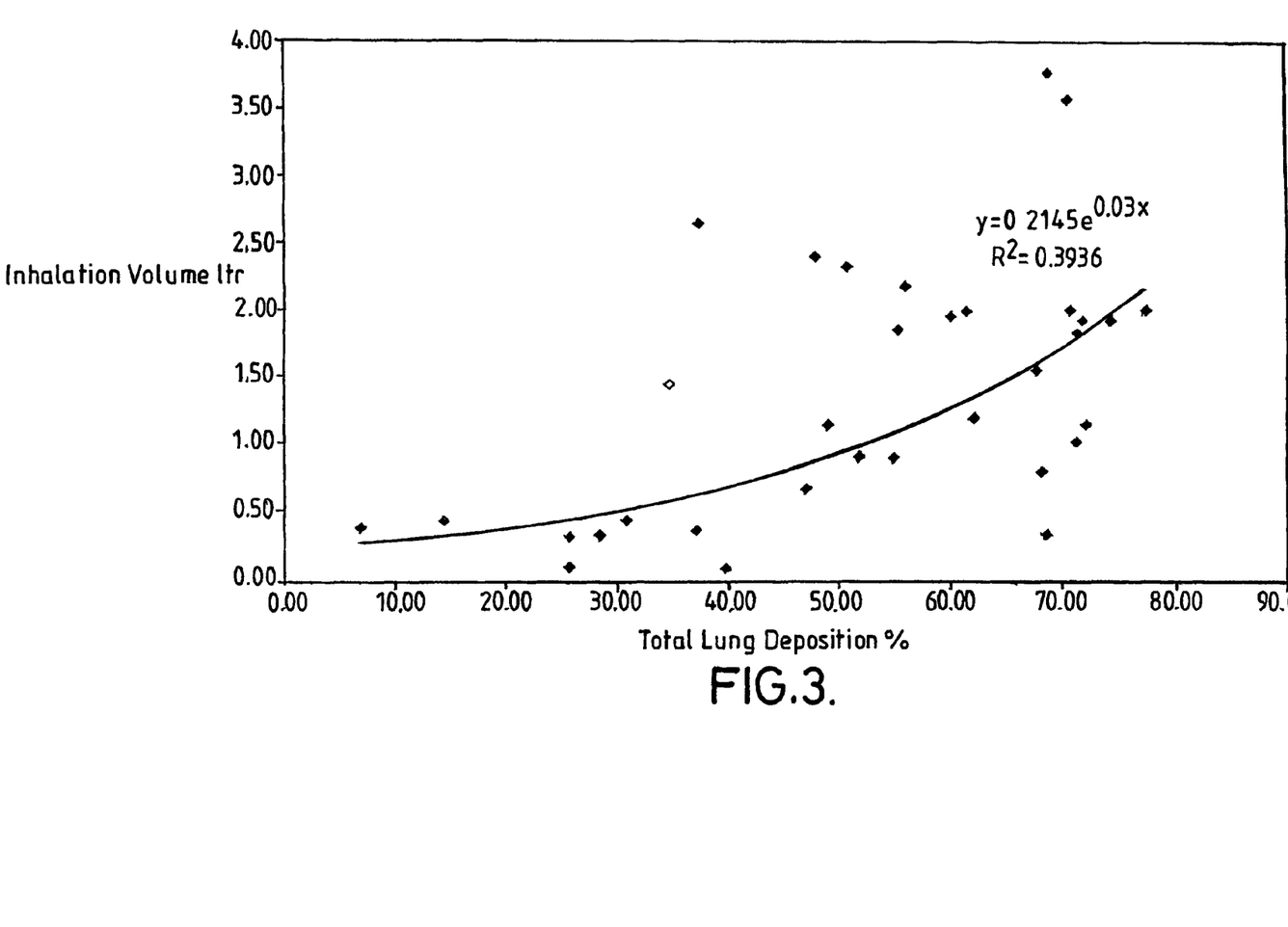
FIG. 3 is a graph plotting the inhalation volume against the total lung deposition.
Figure 4:
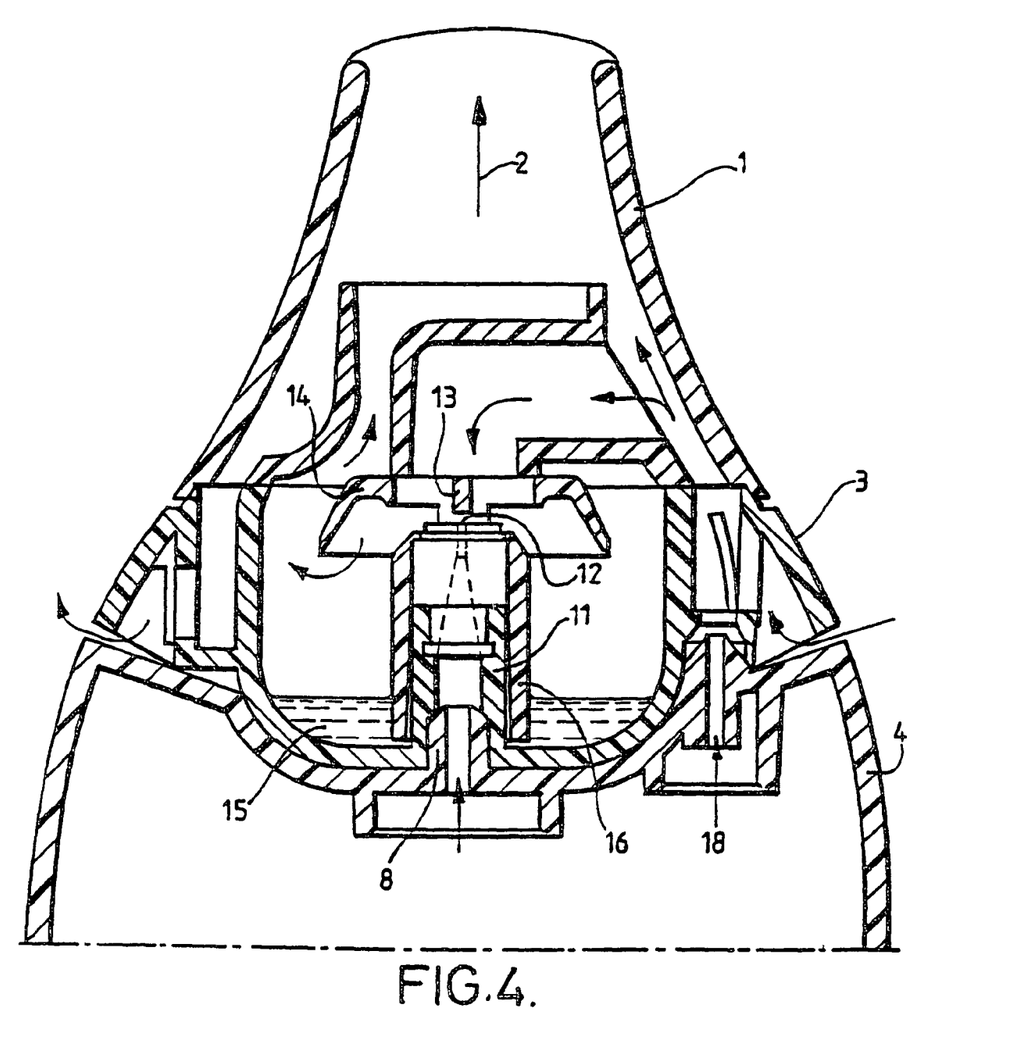
FIG. 4 is a schematic view of a nebulizer according to the present invention.

A scintigraphic evaluation of the patients was carried out in order to identify how much of the radio labelled aerosol remained in the lungs of the patients. The results from both systems were analysed with respect to the patients breathing parameters. The results of the experiment are shown in FIGS. 1, 2 and 3. In FIG. 1, the total residence time of the drug within the lungs is plotted against the total lung deposition as a percentage of the total aerosol delivered. It will be seen clearly that lung deposition increases with the total residence time. For example, a total residence time of 2 seconds is likely to result in less than 30% of the aerosol being deposited in the lungs, whereas doubling the residence time to 4 seconds will typically give a total lung deposition of more than 40%. By the time the total residence time reaches 12 seconds, the lung deposition reaches about two thirds of the aerosol delivered.

FIG. 2 is a graph in which the aerosol hold time (Halolite System) and breath hold time (Akita System) is plotted against the exhaled filter fraction. The exhaled fraction is reduced with increasing aerosol or breath hold time. It indicated that for an aerosol or breath hold time in the order of 1 second, exhaled losses are in the region of 15-20% but if the aerosol or breath hold time is increased to 2 seconds the losses are reduced to 10%. Increasing the aerosol or breath hold time allows more time for the aerosol to deposit in the lung, as the principal method of deposition for particles of this size is sedimentation, which is time dependent.

Figure 5:
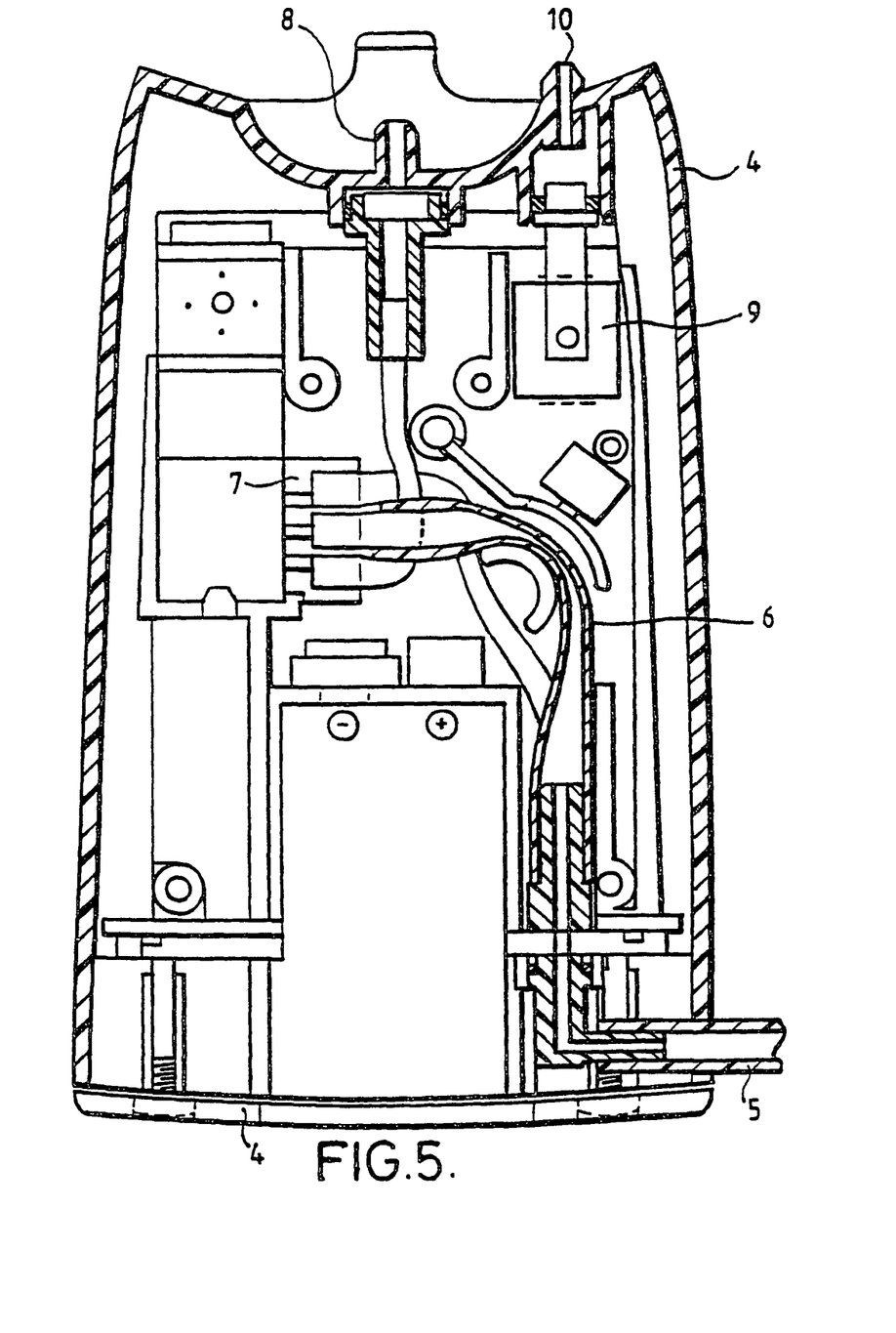
FIG. 5 is a second view of the nebulizer of FIG. 4.

During the experiment, the volume of each person's inhalation was also measured, and this inhalation volume is plotted against the total lung deposition as a percentage of the total amount of the aerosol delivered in a graph in FIG. 3. From the graph, it will be seen that there is a general increase in lung deposition as the inhalation volume increases. To ensure a minimum deposition efficiency of about 50%, a minimum inhalation volume of about 1 liter is required.

The overall conclusion of this experiment is that the longer the aerosol is resident within the lungs, the higher the total lung deposition. This can be achieved by the patient holding his breath following inhalation, by increasing the total inhalation time of the patient, and by the use of an aerosol hold period.

Description Of Preferred Embodiment

This invention applies, amongst other things, to nebulizers of the type which generate pulses of atomisation, as in the prior art nebuliser described above. The invention is not, however, limited to any particular nebulizer, but may be applied to other nebulizers or to other drug delivery devices such as spacers.

Extending the proportion of the inhalation of the patient in which atomisation takes place above 50%, as is used in the Halolite, results in the patient receiving their treatment faster since it will take fewer breaths to deliver the required volume of medication. However, to maintain a satisfactory lung residence time for the medication, delivery of the medication must stop some time before the patient stops inhaling so that the medication has a minimum residence time, preferably of at least half a second, most preferably about one second in duration. This residence time is referred to as the aerosol hold period. However, it is preferred that the aerosol hold period is never shorter than 50% of the predicted duration of inhalation. Treatment time can therefore be minimised while the therapeutic effects are maintained.

FIGS. 4 and 5 of this application show a suitable nebuliser based on the Halolite. Referring to FIG. 4, a mouthpiece 1 is shown through which a patient inhales the direction of arrow 2. Below the mouthpiece 1 is a removable atomising section 3 which, in turn, rests on a base 4.

The base 4 is shown in more detail in FIG. 5. The base 4 includes an inlet 5 through which air is supplied under pressure from a compressor (not shown). The pressurized air is led via a tube 6 to a manifold 7 which controls the flow of pressurized air to an air outlet 8 which directs air into the atomising section 3 shown in FIG. 4. The base 4 also includes a pressure sensor 9 which detects the pressure within the atomising section 3 via aport 10.

Referring again to FIG. 4, air under pressure passes through the air outlet 8 of the base 4 and is conducted through a tubular post 11 to an atomiser nozzle 12 out of which the air issues under pressure. A deflector 13 is located in the path of the pressurised air issuing from the nozzle 12 so that the pressurized air is deflected laterally so as to pass beneath a baffle 14. The passage of the pressurized air across the top of the tubular post 11 causes medication 15 to be drawn up between the outer surface of the tubular post 11 and the inner surface of a sleeve 16 which surrounds the tubular post 11. The medication 15 is atomised in the stream of air, and carried away in the stream of air below the rim of the baffle and up through the mouthpiece 1 to a patient.

The pressure sensor 9 in the base 4 monitors the breathing pattern of a patient, and on the basis of the breathing pattern, the manifold 7 is controlled by a processor (not shown) to supply pressurized air to the atomising section 3 only during part of an inhalation of a user. The processor calculates the length of the pulse of atomization.

Example of Calculations

A preferred example of the calculations carried out will now be described. Where there is adequate tidal volume, and sufficient time between the end of aerosol generation and the start of exhalation, the pulse duration can be extended from the 50% of the prior art Halolite product without significantly affecting the amount aerosol exhaled. Firstly, a calculation can be made to find the tidal volume ($TV_{calc}$).

One way in which this can be done is by multiplying the duration of inspiration measured by the sensor 9 by the peak inhalation flow measured by the sensor 9 and then by a constant which is set to be about 0.7.

Another, preferred, way in which the tidal volume ($TV_{calc}$) is found is carried out on a breath by breath basis so as to calculate, for example from the previous three breaths, an average inhalation volume for the next breath. The patient's inspiratory flow is monitored continuously, typically every 10 ms and this is integrated over the duration of inspiration of the patient to derive the tidal volume of the patient.

GB 2343122A discloses a nebulizer and also discloses these two calculations of the volume of inspiration. We hereby incorporate all of the details of these calculations from that document herein by this reference.

If the calculated tidal volume ($TV_{calc}$) is less than a tidal volume limit, then the processor will control the aerosol generator to generate an aerosol simply during the first 50% of the inhalation phase. In this case, the tidal volume limit is the minimum tidal volume required to extend to the pulse time above 50% of the inhalation period, and is set to about 1 liter in this embodiment, although other volumes could be selected.

If the calculated tidal volume ($TV_{calc}$) is more than or equal to the tidal volume limit, then the processor will carry out a calculation whereby the pre-set time before the person is expected to inhale is subtracted from the expected duration of inhalation to define the pulse length by which the processor controls the aerosol generator to generate an aerosol. For example, if the pre-set time is one second, and the expected duration of inhalation of the person is four seconds, then an aerosol will be generated for three seconds. Other pre-set times may also be appropriate. For example it could be in the range of 0.5 to 2 seconds, or in a narrower range at 0.75 to 1.5 seconds.

The invention also relates to other drug delivery apparatus, such as spacers in which a dose of a drug in droplet or powder form is released into a spacer chamber or holding chamber from which the patient inhales. These are most appropriate for elderly patients or children who have difficulty in using a multi-dose inhaler or dry powder inhaler, for example, because they have trouble co-ordinating the release of the drug with the beginning of inhalation, or because their inhalation flow rates are too small. For example, spacers are disclosed in International patent publication number WO 96/13294, the contents of which are hereby imported by reference.

The length of the atomisation pulse is dependent upon the patient's inspiratory tidal volume. The nebuliser must therefore measure the patient's tidal volume, preferably on a breath by breath basis so as to calculate, for example from the previous three or four breaths, an average inhalation volume for the next breath.

A timer is included in the nebuliser connected to the pressure sensor 9 (shown in FIG. 5) in order to measure the duration of inspiration. A memory is also included in the nebulizer in which is stored one or more of the following:
1. the duration of inhalation of a number of recent inhalations;
2. the average duration of inhalation of a number of recent inhalations;
3. the pre-set time;
4. the breathing threshold or
5. programming instructions on the operation of the apparatus.

According to one form of the invention, the patient's inspiratory flow is monitored continuously, typically every ten milliseconds, and this is integrated over the inspiratory duration.

In view of the fact that the nebuliser adapts to the breathing pattern of a patient, when the patient starts breathing, no atomization takes place during the first three or four breaths. Those first three or four breaths are used to analyse the breathing pattern of the patient. The flow rate of those breaths are measured, and from this, the average duration of the inhalation phase of the breaths is calculated. The average duration of inhalation is then used in the calculation to determine the pulse length of atomisation during the subsequent breath. In addition, as the patient continues to breathe in and out, the average duration of inhalation is calculated using the breaths immediately proceeding the breath that is being predicted. Thus, if a patient's breathing pattern improves during treatment, the nebuliser will adapt to this change in order to optimise the dose administered during each breath.

Further Embodiment

Figures 6, 7:
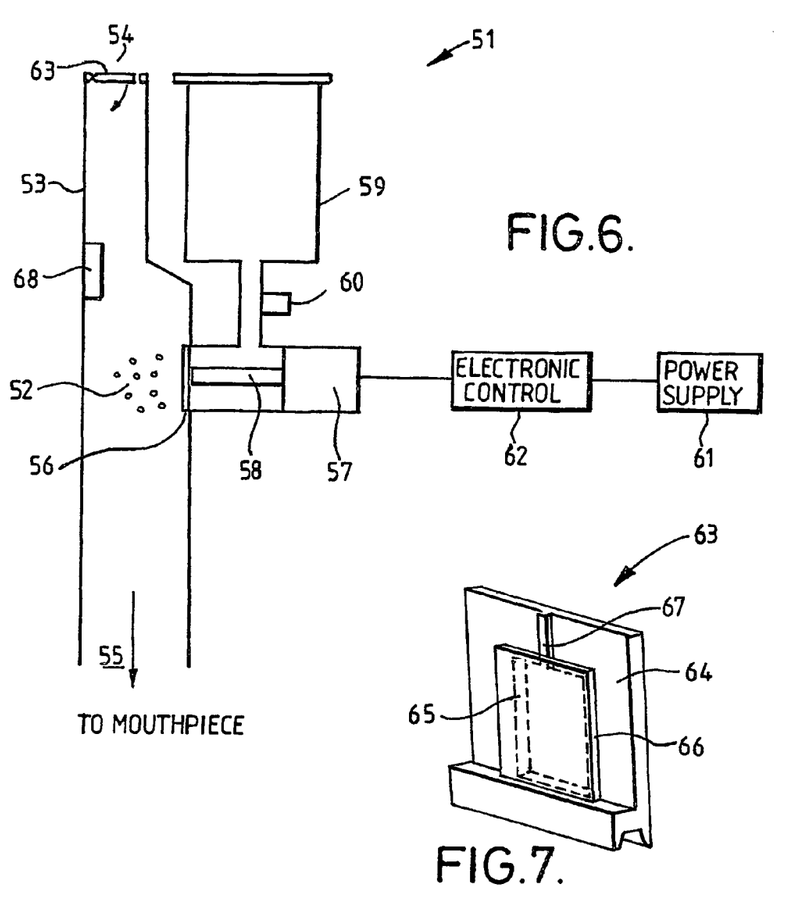
FIG. 6 is a schematic view of a nebulizer according to a second embodiment of the invention.
FIG. 7 is a perspective view of an airflow regulator of the embodiment shown in FIG. 6.

Referring now to FIG. 6, a drug delivery apparatus is shown which is a mesh type nebulizer 51 for generating an aerosol indicated generally at 52 in a passageway 53. The passageway 53 has an inlet 54 through which air enters it, and at its opposite end 55 the air passing through the passageway 53 is led to a mouthpiece or the like (not shown). During operation of the nebulizer 51, the aerosol 52 is entrained in the airflow leading to the mouthpiece. Nebulization takes place by a drug being forced through a mesh plate 56 by using an ultrasonic transducer 57 which drives a horn 58 to vibrate in the region of the mesh plate 56. The horn 58 is located close to the rear face of the mesh plate 56 and is caused to vibrate by the ultrasonic transducer 57, whereby the aerosol 52 is generated from the front face of the mesh plate 56. The substance to be atomised into an aerosol 52 is in fluid contact with the rear face of the mesh plate 56 and it is this that is driven through the holes of the mesh plate 56 by the vibrating horn 58.

During each treatment, a certain volume of the substance to be atomised is located in a reservoir 59 which is located above the mesh plate 56 in which to feed the substance to be atomised to its rear face. A fluid sensor 60 is located between the reservoir 59 and the mesh plate 56 such that once the substance to be atomised has substantially all been aerosolized, this is detected so that the ultrasonic transducer 57 may be switched off at the end of treatment.

A power supply 61 is used to power the atomiser since power is required to drive aerosolization. An electronic controller 62 controls the ultrasonic transducer 57 so that, for example, once the fluid sensor 60 senses that there is no liquid remaining to be atomised, the ultrasonic transducer 57 will be switched off. In addition, a more sophisticated control device can be used here such that the patient's breathing is measured, and atomisation only occurs during the inhalation part of a patient's breathing pattern.

An airflow regulator 63 is located in the passageway 53. This is shown in more detail in FIG. 7 from which it will be seen that the regulator 63 includes a frame 64 having an interior edge 65 (shown in dotted lines) which defines an aperture through which air must pass if it is to enter the passageway 53. A resilient flap 66 is located in front of the aperture located in the frame 64, and a rib 67 lying on the frame 64 acts as a spacer to prevent the flap 66 from completely closing the aperture. The flap 66 is typically made of a resilient silicone material. This means that any airflow through the regulator 63 which passes through the aperture and then against the flap 66 will cause the flap 66 to be deflected away from the frame 64 allowing the air to pass relatively freely. However, airflow passing the opposite way will cause the flap 66 to close, and the aperture will be severely restricted allowing a limited airflow to pass. The resilient nature of the flap will tend to offer more resistance to the airflow the greater the pressure difference on the opposite sides of the frame 64. This airflow regulator, therefore, limits the rate at which air passes through the passageway 53 towards the mouthpiece and has the effect of lengthening the duration of inhalation which allows longer pulses of aerosol to be delivered. This will reduce the time it takes to deliver a volume of a drug.

The nebulizer also includes an airflow detector 68 which is able to measure both the direction of airflow through the passageway 53 and the velocity of the airflow. In this embodiment, it is indicated to be located within the passageway 53, but could be located in various other positions, even in the mouthpiece. The detector 68 may be any one of a variety of different types of detector, such as a temperature sensor, a pressure sensor, a microphone type sensor or a mechanical sensor which is deflected by the airflow. The type of sensor used is not an important factor in this invention.

Figure 8:
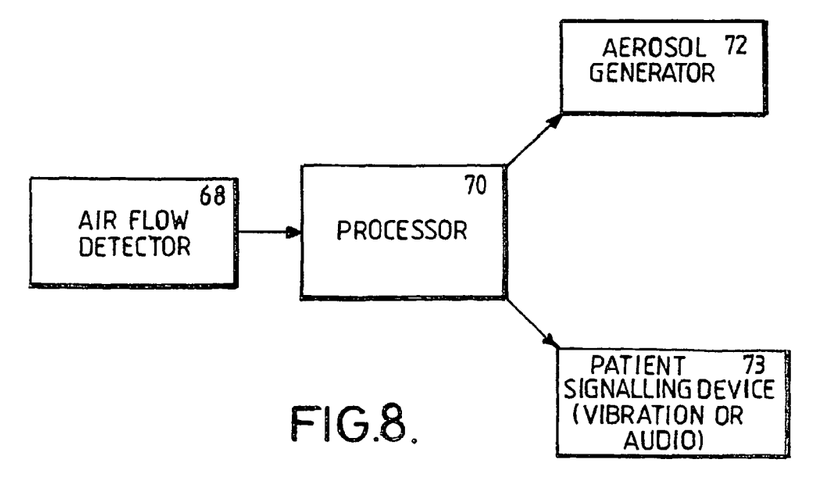
FIG. 8 is a block diagram showing how the nebulizer is controlled, and how the patient is signalled.

FIG. 8 shows the arrangement of the nebulizer in block diagram form. From it, one block refers to the airflow detector 68 shown in FIG. 6. The output from the detector 68 is passed to a processor 70 which controls the aerosol generator 72 and a patient signalling device 73. The processor 70 will include the electronic control 62 shown in FIG. 6, as well as other elements. The aerosol generator 72 refers to a combination of the mesh plate 56, the ultrasonic transducer 57, the horn 58 and the reservoir 59 in the nebulizer 51 shown in FIG. 6. The patient signalling device 73 is not shown in FIG. 6, but is some form of device which generates feedback signals for the patient when inhalation is detected and when treatment is complete. According to one arrangement, this could be a vibrator device which causes the nebulizer 51 to gently vibrate. Alternatively, it can be an audio device which uses sounds to signal to the patient. It could even be a visual device where the patient is signalled on the basis of visual signals which may be lights or an LCD screen. The signalling device 73 could be a combination of these systems.

The basic operation of this nebulizer will now be described. Firstly, the patient will pour a certain volume of the substance to be atomised into the reservoir 59. The reservoir 59 may be sized such that it will exactly hold the appropriate volume of the substance that is required. The patient can then begin to breathe in and out through the mouthpiece. Upon commencement of inhalation, the airflow detector 68 will detect the commencement of inhalation, and the electronic control 62 will cause the ultrasonic transducer 57 to vibrate, thereby driving the horn 58 to cause aerosolization of the substance to be atomised. As the substance is aerosolized, the reservoir 59 empties, and once the level of the substance drops below the fluid sensor 60, the electronic control 62 switches off the ultrasonic transducer.

During inhalation, the airflow regulator 63 operates to regulate the speed of air passing through the passageway 53 and to the patient, thereby lengthening the patient's inhalation phase.

The nebulizer will only deliver aerosol laden with the aerosol 52 during part of each inhalation by the patient. The nebulizer will be arranged such that there is a pre-set period of time at the end of each inhalation of the patient during which the drug is not delivered. It is, therefore, important that the nebulizer is able to estimate the duration of each inhalation phase. Therefore, when the patient first uses the device, he will breathe in and out, and the commencement and end of inhalation will be measured over a number of breaths typically three or four, and an average breath length calculated. This average inhalation length is used as the estimate for the subsequent duration of inhalation.

A calculation can then be made by the processor 70 to subtract the aerosol hold period from the estimated inhalation length. This will give the period over which the aerosol can be delivered to the patient such that the aerosol hold period during which the patient continues to inhale without any aerosol being inhaled, should approximate the desired pre-set aerosol hold period. As such, the processor 70 will control the aerosol generator 72 to generate an aerosol of the drug from the commencement of the inhalation to the beginning of the aerosol hold period when it is switched off by the processor 70. The full calculation is explained in more detail above with respect to the preferred embodiment.

Since the symptoms of the patient can vary over time, both from treatment to treatment, and even during a single treatment, by regularly recalculating the estimated period of inhalation, the nebulizer remains optimised for that patient at that particular time. In fact, in the preferred embodiment, the estimated inhalation period is recalculated on every breath by taking an average of the last few inhalation periods.

During exhalation, the exhaled air might be exhausted from an outlet in the mouthpiece, or alternatively might flow back up the passageway 53 towards the airflow regulator 63 which will open to allow the air to be exhausted freely. It is preferable to locate the airflow detector 68 as close to the mouthpiece as possible, and where the exhaled air is exhausted from an outlet in the mouthpiece, it will normally be appropriate to locate the airflow detector 68 within the mouthpiece.

The use of an airflow regulator may be preferred since it lengthens the period of inhalation which allows longer pulses of aerosol to be delivered, and this reduces treatment times.

Also, the airflow regulator 63 may be located anywhere in the device where it will restrict the airflow leading to the patient. However, it is preferred that it is located upstream of the point at which the aerosol is generated during inhalation. That way, the aerosol will not be removed from the airstream by the constriction caused by the airflow regulator 63.

It will be appreciated that, although a mesh type nebulizer is used in the device shown in FIGS. 6 and 7, other types of nebulizer may be equally appropriate. What is important is the adaptation of the nebulizer to the patient's actual breathing pattern.

The invention claimed is:

1. A drug delivery apparatus for releasing a drug in aerosolized form into an inhaled airstream of a person, the drug delivery apparatus comprising:
   a processor programmed
      to obtain an expected inhalation length;
      to obtain an end inhalation amount of time that corresponds to a specific minimum lung residence time such that drug delivered to the person at least the end inhalation amount of time before the end of an inhalation will have an aerosol hold within the lungs of the person for at least the minimum lung residence time, wherein the specific minimum lung residence time is 0.5 seconds;
      to determine a pulse length for a pulse of release of the drug based on a subtraction of the end inhalation amount of time from the expected inhalation length; and
      to release the pulse of the drug for the pulse length so that the pulse ends the end inhalation amount of time before the obtained expected inhalation length expires to effect the aerosol hold of the drug delivered in the pulse in which the minimum lung residence time of the drug delivered in the pulse is at least 0.5 second;
   wherein the processor is programmed to release the pulse of the drug for a pulse length so that the pulse is for a pre-set proportion of an expected period of inhalation in the event that a breathing threshold is not reached.

2. A drug delivery apparatus according to claim 1, wherein the aerosol hold gives a minimum lung residence time of about 1 second.

3. A drug delivery apparatus according to claim 1, wherein the breathing threshold is a minimum expected duration of inhalation.

4. A drug delivery apparatus according to claim 3, wherein the minimum expected duration of inhalation is about twice the end inhalation amount of time before the person is expected to stop inhaling when the pulse ends.

5. A drug delivery apparatus according to claim 1, wherein the breathing threshold is a minimum tidal volume.

6. A drug delivery apparatus according to claim 5, wherein the breathing threshold is about 1 liter.

7. The drug delivery apparatus according to claim 1, wherein the end inhalation amount of time is between 0.75 seconds and 1.5 seconds.

8. The drug delivery apparatus according to claim 1, wherein the end inhalation amount of time is about 1 second.

9. A drug delivery apparatus according to claim 1, wherein the drug delivery device further comprises an airflow sensor which senses the person's inhaled airstream.

10. A drug delivery apparatus according to claim 9, wherein the drug delivery device further comprises a memory for holding any one or more of the following:
   (i) a duration of inhalation of a number of recent inhalations;
   (ii) an average duration of inhalation of a number of recent inhalations;
   (iii) the end inhalation amount of time before the obtained expected inhalation length expires;
   (iv) a breathing threshold;
   (v) programming instructions on an operation of the apparatus.

11. A drug delivery apparatus according to claim 1, wherein the processor controls an operation of the apparatus.

12. A drug delivery apparatus according to claim 1, wherein the apparatus further comprises a timer.

13. A method of controlling a drug delivery apparatus of the type for releasing a drug in aerosolized form into an inhaled airstream of a person, the method comprising:
   determining, using a processor, an expected inhalation length;
   determining an end inhalation amount of time that corresponds to a specific minimum lung residence time such that drug delivered to the person at least the end inhalation amount of time before the end of an inhalation will have an aerosol hold within the lungs of the person for at least the minimum lung residence time, wherein the specific minimum lung residence time is 0.5 seconds;

determining a pulse length for a pulse of release of the drug based on a subtraction of the end inhalation amount of time from the expected inhalation length; and controlling the apparatus, using the processor, to release the pulse of the drug in aerosolized form into the inhaled airstream of a person for the pulse length so that the pulse ends the end inhalation amount of time before the determined expected inhalation length expires to effect the aerosol hold of the drug delivered in the pulse in which the minimum lung residence time of the drug delivered in the pulse is at least 0.5 second;

further including a breathing threshold, wherein the pulse of the drug is released for a pulse length so that the pulse is for a pre-set proportion of an expected period of inhalation in the event that the breathing threshold is not reached.

14. A method according to claim 13, wherein the aerosol hold gives a minimum lung residence time of about 1 second.

15. A method according to claim 13, wherein the method further comprises creating an estimate of the duration of inhalation.

16. A method according to claim 15, wherein creating an estimate of the duration of inhalation includes timing the duration of inhalation of one or more earlier breaths.

17. A method according to claim 13, wherein the breathing threshold is a minimum expected duration of inhalation.

18. A method according to claim 17, wherein the minimum expected duration of inhalation is about twice the end inhalation amount of time before the person is expected to stop inhaling when the pulse ends.

19. A method according to claim 13, wherein the breathing threshold is a minimum tidal volume during inhalation.

20. A method according to claim 19, wherein the breathing threshold is about 1 liter.

21. A method according to claim 13, wherein the end inhalation amount of time is between 0.75 and 1.5 seconds.

22. A method according to claim 13, wherein the end inhalation amount of time is about 1 second.

23. A method according to claim 13, further comprising sensing the person's inhaled airstream using an airflow sensor.

24. A method according to claim 13, wherein the method further comprises storing any one or more of the following in memory:
   (i) a duration of inhalation of a number of recent inhalations;
   (ii) an average duration of inhalation of a number of recent inhalations;
   (iii) the end inhalation amount of time before the obtained expected inhalation length expires;
   (iv) a breathing threshold;
   (v) programming instructions on an operation of the apparatus.

* * * * *